United States Patent
Yang (10) Patent No.: US 8,663,181 B2
(45) Date of Patent: Mar. 4, 2014

(54) DISPOSABLE URINE BAG DEVICE

(76) Inventor: Kuo-Huang Yang, Taipei (TW)

( * ) Notice: Subject to any disclaimer, the term of this patent is extended or adjusted under 35 U.S.C. 154(b) by 259 days.

(21) Appl. No.: 12/897,410

(22) Filed: Oct. 4, 2010

(65) Prior Publication Data

US 2011/0087183 A1  Apr. 14, 2011

(30) Foreign Application Priority Data

Oct. 9, 2009 (TW) ............................... 98134363 A
Jul. 29, 2010 (TW) ............................... 99125039 A (51) Int. Cl.
*A61F 5/44* (2006.01)
*A47K 11/00* (2006.01)
*A61F 5/451* (2006.01)
*A61F 5/455* (2006.01)
*A47K 11/12* (2006.01)

(52) U.S. Cl.
USPC ........... 604/347; 604/317; 604/327; 604/329; 604/330; 604/331; 604/346; 4/144.1; 4/144.2; 4/144.3; 600/300; 600/573; 600/574

(58) Field of Classification Search
USPC ............... 604/317–416; 4/449, 144.1–144.4, 4/258–259, 267, 271, 274, 285; 141/311 R–386, 311 A; 220/600–601, 220/660–661, 676, 694, 752, 755–758, 220/761–764, 767–769, 771–772; 224/217; 383/1–2, 7, 11, 33, 35–36, 210–211, 383/41, 61.1, 61.3, 66–67, 78, 81–93, 383/97–103, 906–907; 600/300, 573–584
See application file for complete search history.

(56) References Cited

U.S. PATENT DOCUMENTS

| | | | | |
|---|---|---|---|---|
| 2,548,149 A | * | 4/1951 | Fowler, Jr. | 604/347 |
| 2,690,568 A | * | 10/1954 | Willis | 4/144.4 |
| 2,855,607 A | * | 10/1958 | Sullivan | 4/144.2 |
| 3,200,415 A | | 8/1965 | Breece, Jr. | |
| 3,253,593 A | | 5/1966 | Cronin, Jr. | |
| 3,403,410 A | * | 10/1968 | Benzel et al. | 4/144.2 |
| 3,815,581 A | * | 6/1974 | Levin | 600/574 |
| 4,054,957 A | * | 10/1977 | Diamond | 4/144.2 |
| 4,500,314 A | * | 2/1985 | Brendling | 604/346 |

(Continued)

FOREIGN PATENT DOCUMENTS

CN  2449680 Y  9/2001
CN  1270677 C  8/2006

(Continued)

*Primary Examiner* — Loan Thanh
*Assistant Examiner* — Joshua Lee
(74) *Attorney, Agent, or Firm* — Rosenberg, Klein & Lee (57) ABSTRACT

A disposable urine bag device includes a bag having an open top; and two cuff-like supporting members formed on two sides of the open top of the bag, wherein two fingers are allowed to insert into the supporting members to position the bag and adjust size of the open top of the bag. Moreover, a zipper is provided just below the open top of the bag for sealing the bag. Hence, after use an individual may seal the bag for disposal in an environment without the provision of public toilet. Further, an opening is provided on a sidewall of the bag for urine drainage. A woman may urinate by means of the disposable urine bag device while in standing position. Furthermore, a valve is mounted on the opening so that collected urine may drain via the valve. The collected urine may be used for health examination by hospitals.

12 Claims, 11 Drawing Sheets

(56) References Cited

U.S. PATENT DOCUMENTS

| | | | |
|---|---|---|---|
| 4,681,573 A * | 7/1987 | McGovern et al. | 604/329 |
| 4,731,064 A * | 3/1988 | Heyden | 604/352 |
| 4,863,448 A * | 9/1989 | Berg | 604/349 |
| 5,004,463 A * | 4/1991 | Nigay | 604/329 |
| 5,065,459 A * | 11/1991 | Tjahaja et al. | 4/144.2 |
| 5,235,705 A * | 8/1993 | Belisle | 4/144.3 |
| 5,370,637 A | 12/1994 | Brodeur | |
| 6,213,990 B1 | 4/2001 | Roempke | |
| 6,345,911 B1 | 2/2002 | Young | |
| 6,922,852 B1 * | 8/2005 | Blum | 4/144.4 |
| 7,131,149 B2 | 11/2006 | Langford | |
| 7,181,781 B1 | 2/2007 | Trabold | |
| 7,462,171 B2 * | 12/2008 | Salvadori et al. | 604/327 |
| 2002/0193762 A1 * | 12/2002 | Suydam | 604/327 |
| 2004/0223667 A1 * | 11/2004 | Shah et al. | 383/103 |
| 2007/0255239 A1 * | 11/2007 | Hataya | 604/319 |

FOREIGN PATENT DOCUMENTS

| | | |
|---|---|---|
| EP | 0549850 A1 | 7/1993 |
| GB | 2336830 A | 11/1999 |
| WO | WO 9203994 A1 | 3/1992 |
| WO | WO 2007050716 A1 | 5/2007 |
| WO | WO 2007138628 A1 | 12/2007 |

* cited by examiner

DISPOSABLE URINE BAG DEVICE

The current application claims foreign priorities to the following two foreign applications.
1. Taiwan, 098134363, filed on Oct. 10, 2009
2. Taiwan, 099125039, filed on Jul. 29, 2010

BACKGROUND OF THE INVENTION

1. Field of Invention

The invention relates to urine collection devices and more particularly to a disposable bag for collecting urine and draining same.

2. Description of Related Art

How to find a public toilet to urinate is always a bothersome thing for people in an outdoor environment. Some people, especially women, do not want to use unhygienic toilet for urination. Instead, they would rather holding back urine. This is not healthy because holding back urine for a long period of time can harm the kidneys.

Additionally, a hospital would provide a paper cup or disposable paper bag to an individual taking health examination so that the individual may use same to collect urine. Next, the individual may pour collected urine into a test tube. However, the hand holding the cup or bag may become dirty by contacting spilled urine if sufficient care is not taken. Moreover, urine is smell and may be spilled during transportation. Further, it is difficult to pouring urine into the test tube since its bore is relatively small.

Thus, it is desirable to provide a novel disposable urine bag device for overcoming above drawbacks experienced by the conventional urine collection devices.

SUMMARY OF THE INVENTION

It is therefore one object of the invention to provide a disposable urine bag device comprising two supporting members formed on two sides of the front portion of the open top of a bag respectively, wherein each supporting member is integrally formed with an upper portion of the bag and two fingers are allowed to move the bag and adjust size of the open top of the bag by controlling the supporting members so as to precisely position the urine bag device closed to the body and aim at the excretory orifices for collecting the excreted urine.

It is another object of the invention to provide a disposable urine bag device comprising a zipper just below the open top so that after use an individual may pull the zipper to close the bag for disposal in an outdoor environment without the provision of public toilet.

It is still another object of the invention to provide a disposable urine bag device comprising a zipper just below the open top and an opening formed on one sidewall of the bag, and a valve mounted on the opening so that collected urine may drain via the valve for examination.

It is a further object of the invention to provide a disposable urine bag device comprising an opening formed on one sidewall of the bag, or a pipe connected to the opening for directing the excreted urine. A woman may use the disposable urine bag device for urination while in standing position without causing contamination of her clothes.

To achieve above and other objects, the invention provides a disposable urine bag device comprising a bag having an open top on the top and two cuff-like supporting members formed on two sides of the front portion of the open top of the bag. The bag comprises two sidewalls which form the bag and a bottom edge which is distant from the open top. The adhesive material is applied on the finger sides of both supporting members in order to let two fingers hold on two sides of open top more effectively, wherein two fingers of an individual are allowed to insert into the supporting members to move the bag and adjust size of the open top of the bag so that it is capable of precisely controlling the size of opening of the top of the bag or positioning the urine bag device closed to the body for accepting excrement passed out of excretory orifices. Moreover, a zipper is provided just below the open top of the bag for sealing the bag. Hence, after use an individual may pull the zipper to close the bag for disposal in an outdoor environment without the provision of public toilet. Further, an opening is provided on a sidewall of the bag for running off the content of the bag, and a valve is mounted on the opening so that collected urine may drain via the valve. It is particularly applicable in urine examination. Alternatively, a pipe can be connected to the opening for directing the excrement.

To achieve above and other objects, the invention provides a disposable urine bag device comprising a bag having an open top with a front portion of higher elevation and a rear portion of lower position and the bag comprises two sidewalls which form the bag and the bottom edge which is distant from the open top; and two cuff-like supporting members formed at a front portion on two sides of the open top of the bag respectively and each supporting member is integrally formed with an upper portion of the bag, wherein each supporting member is at an obtuse angle with respect to a rear portion of the open top of the bag on the side contacted with a human body, two fingers of an individuals are allowed to insert into the supporting members to position the bag and adjust size of the open top of the bag in order to completely cover the excretory orifices of human being.

By utilizing the disposable urine bag device of the invention, it is more easily to utilize and an individual is permitted to hold the device against excretory orifices with sufficient pressure to form a seal. Hence, it can correctly collect the excrement without leaking. An individual, especially a woman, may use the disposable urine bag device to urinate in more situations, even in a standing position or sitting position as in an automobile without being embarrassed.

The above and other objects, features and advantages of the invention will become apparent from the following detailed description taken with the accompanying drawings.

DETAILED DESCRIPTION OF THE INVENTION

Figure 1A:
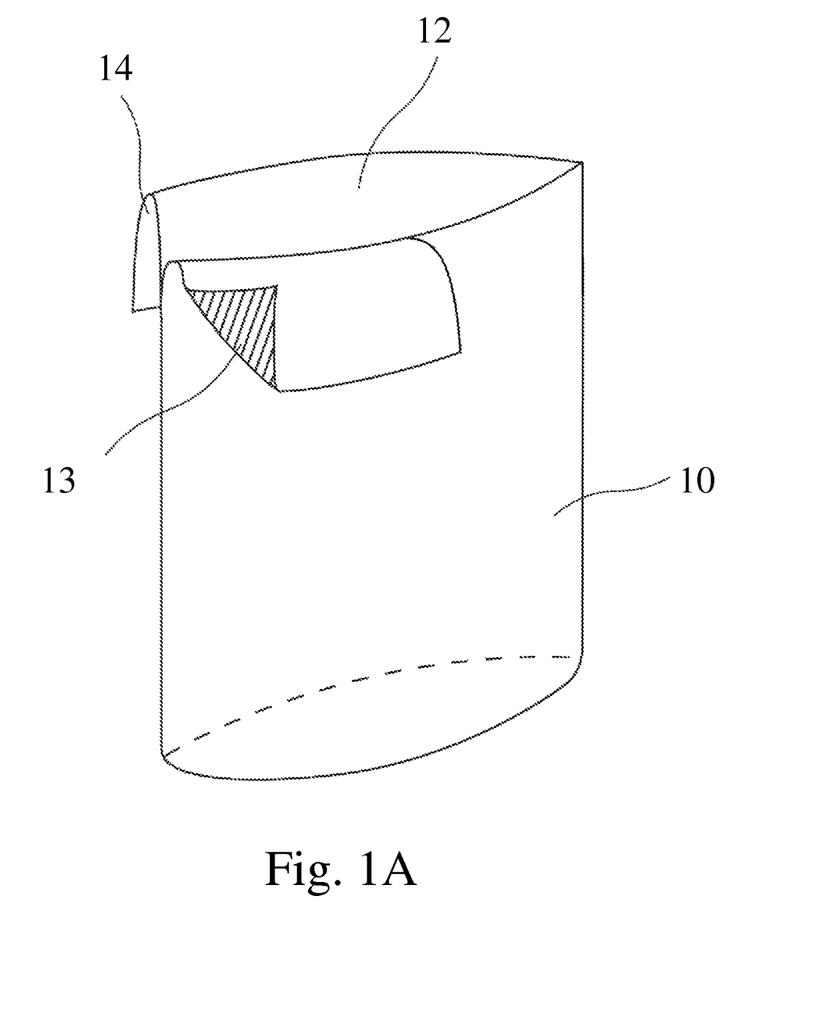
FIGS. 1A and 1B are respectively perspective and environmental views of a disposable urine bag device according to a first embodiment of the invention incorporating a first configuration of supporting members and a first configuration of bag.
Figure 1B:
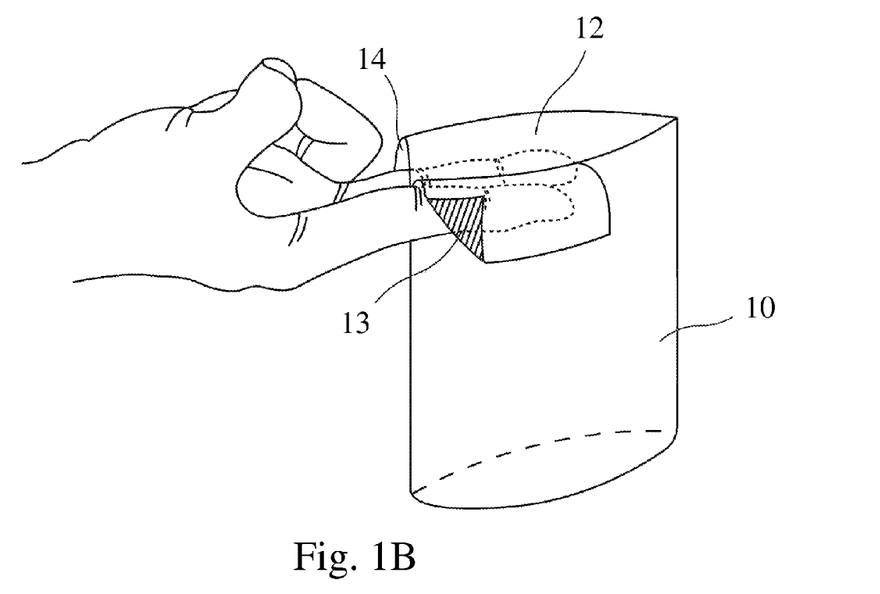

Referring to FIGS. 1A and 1B, a disposable urine bag device in accordance with a first embodiment of the invention comprises a bag 10 made of thermoplastic, paper or other soft materials for easy storage and carriage. On the top of the bag 10 is an open top 12. The bag 10 has two sidewalls which form the bag 10 and a bottom edge which is distant from the open top 12. Two supporting members 14 are located at two sides of the front portion of the open top 12 respectively. It should be noted, each supporting member 14 may be integrally formed with an upper portion of the bag 10. Two fingers are allowed to insert into the supporting members 14 (see FIG. 1B). In the embodiment, each supporting member is a fold, especially a cuff-like fold.

Figure 1C:
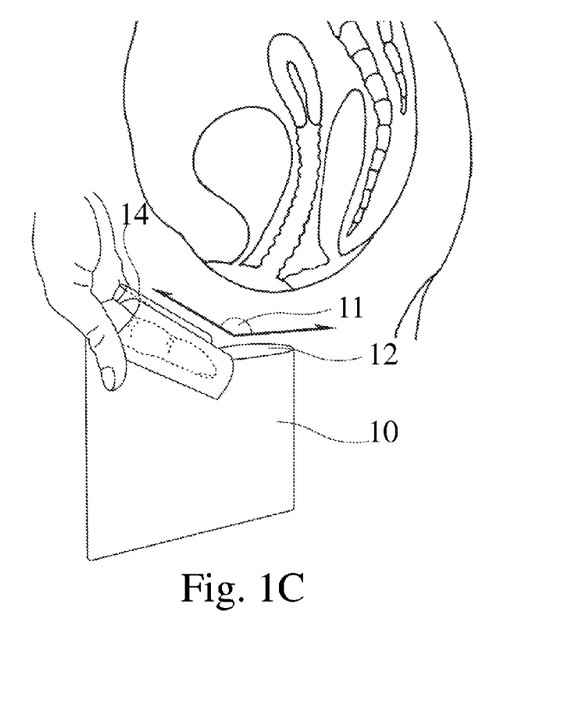
FIG. 1C is an environmental view of a disposable urine bag device according to a second embodiment of the invention.
Figure 1D:
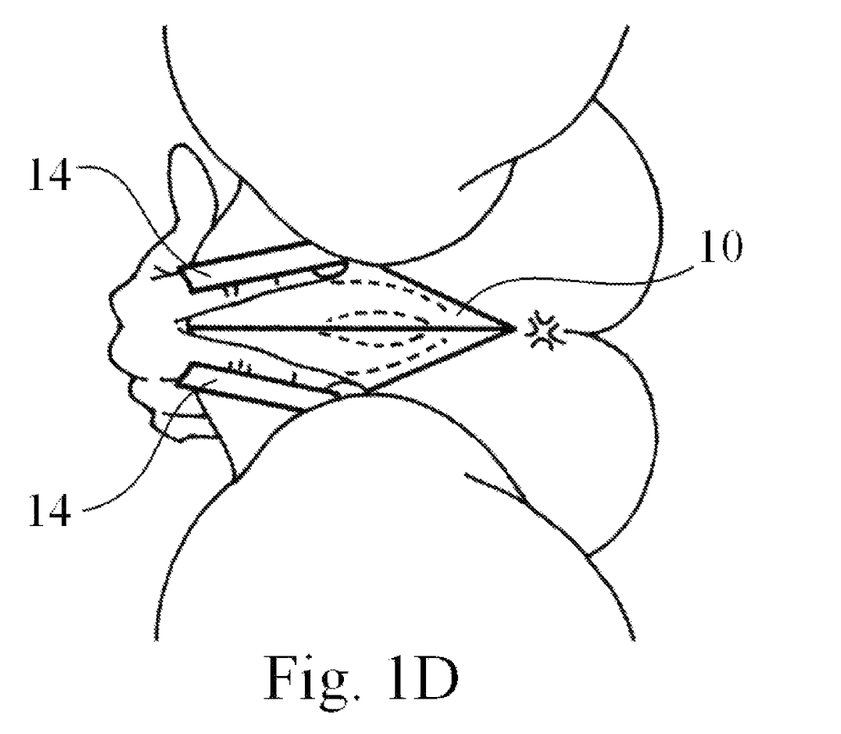
FIG. 1D is a bottom view of a disposable urine bag device according to a second embodiment of the invention.

The adhesive material 13 is applied on the finger sides of both supporting members 14 in order to let two fingers hold on two sides of open top 12 more effectively. Thus, an individual may use the flexible fingers to move the bag 10 and adjust size of the open top 12 of the bag 10 so as to precisely position the urine bag device closed to the body by means of finger touch for collecting excrement excreted out of excretory such as vulva or anus. Urine is prevented from leaking in the collection process due to close contact of the supporting members 14 and the skin. Further, the soft nature of the bag 10 can bring a degree of comfort to an individual in use. Referring to FIG. 1C, a disposable urine bag device according to a second embodiment of the invention is shown. The characteristics of the urine bag device are detailed below. It has a front portion of higher elevation and a rear portion of lower position for the open top 12. The front portion of the open top 12 is toward the fingers and the rear portion of the open top 12 is toward the hip in utilizing. The supporting members 14 are located at two sides of the front portion of the open top 12 respectively, and an obtuse angle 11 exists between the supporting members 14 and the rear portion of the open top 12. The obtuse angle 11 is on the side contacted with a human body and is fit with the outline of the vulva (show as FIG. 1D). It is particularly applicable for women use.

Figure 2A:
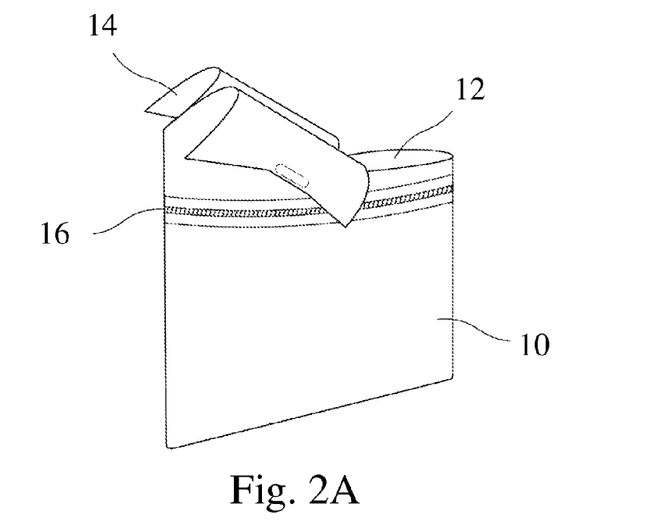
FIGS. 2A to 2B are perspective views of the disposable urine bag device incorporating two configurations of the supporting members according to the invention respectively.
Figure 2B:
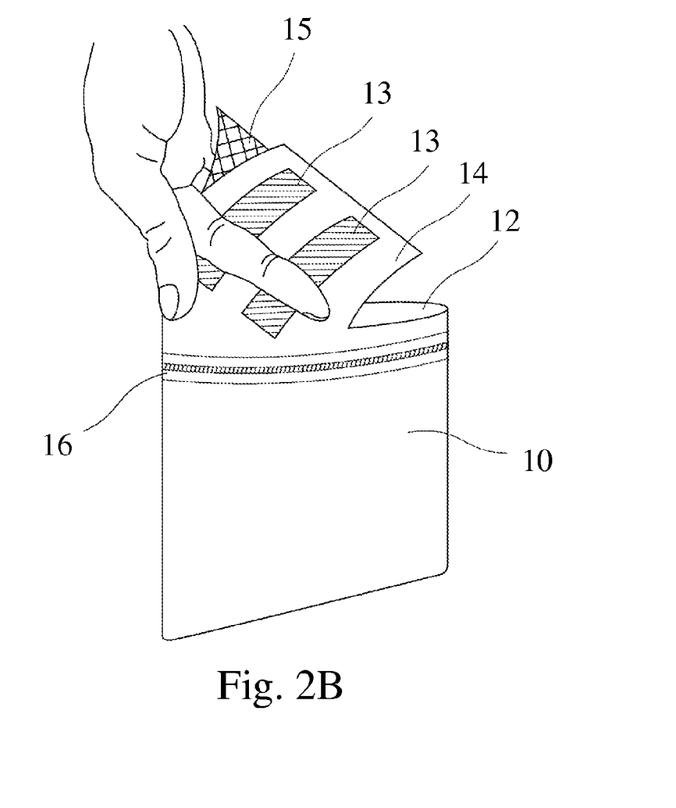
Figure 2C:
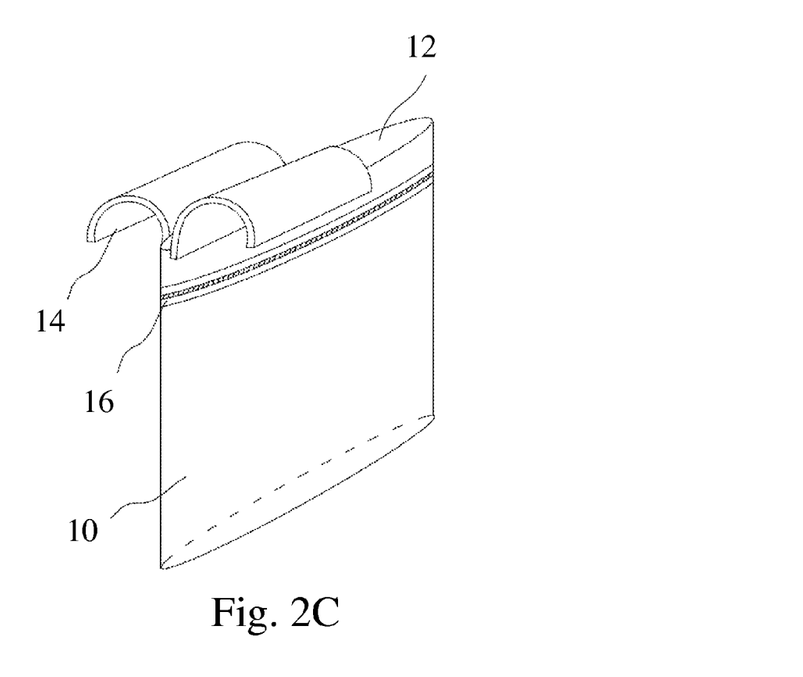
Figure 2D:
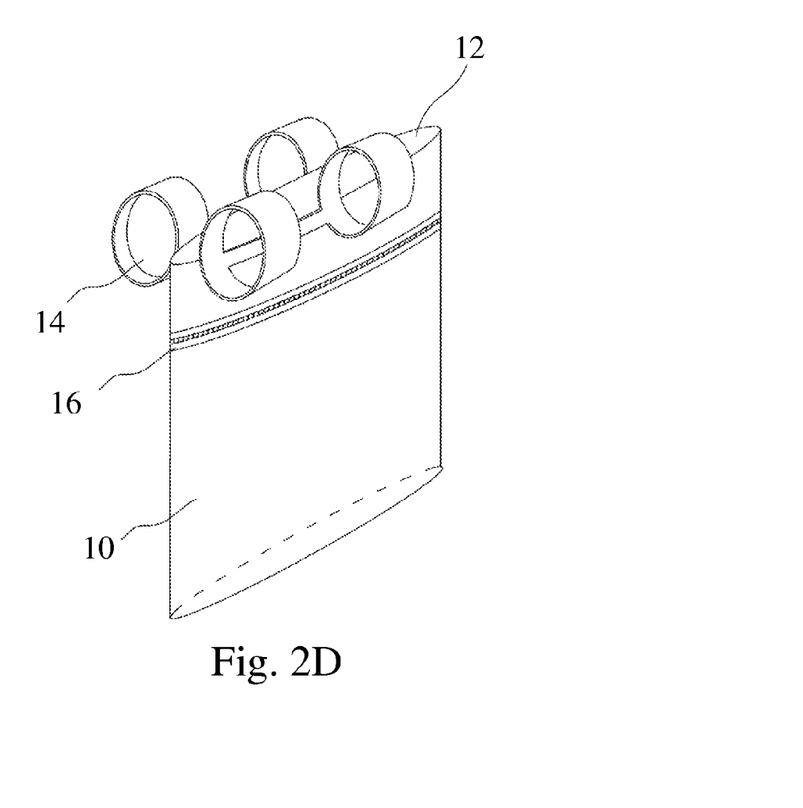
Figure 2E:
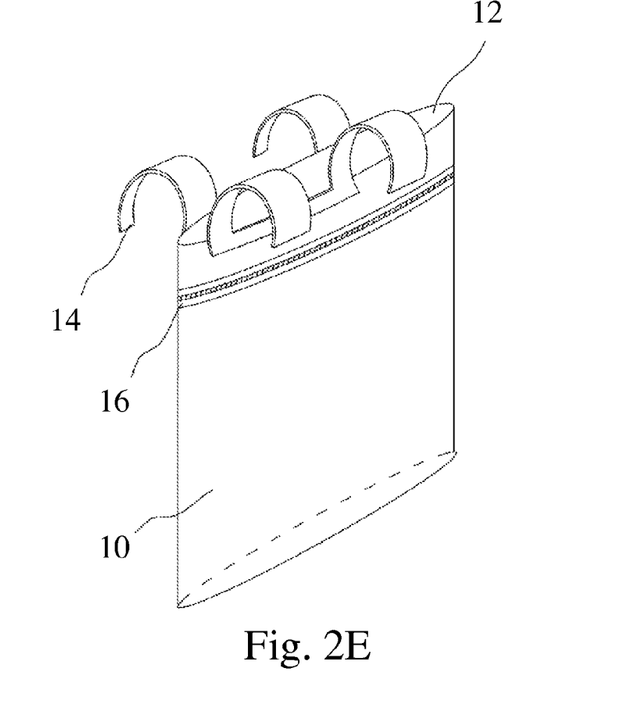
Figure 3A:
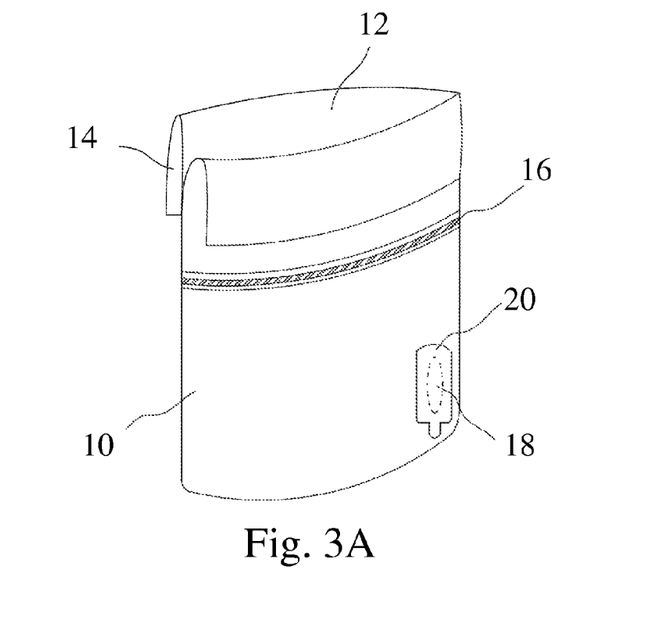
Figure 3B:
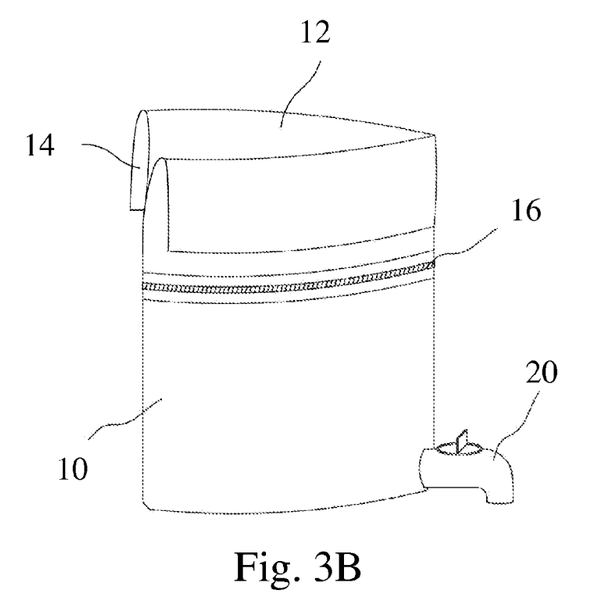
Figure 3C:
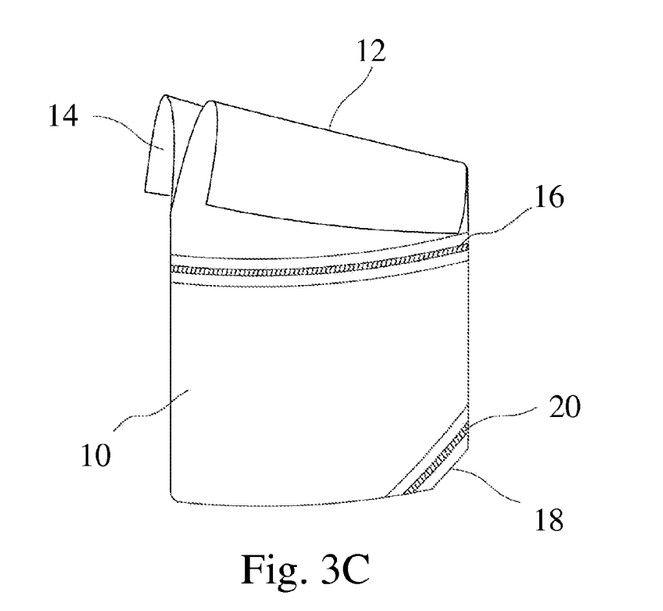
Figure 3D:
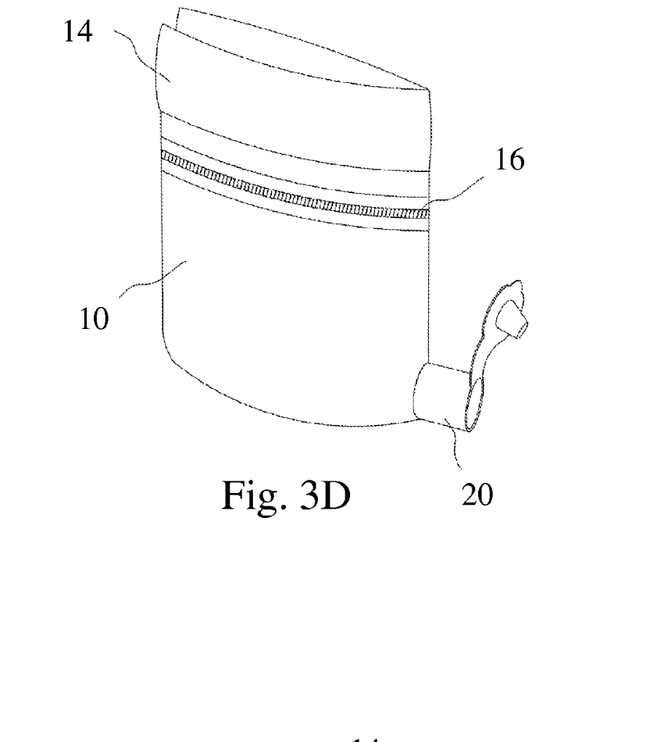
Figure 4:
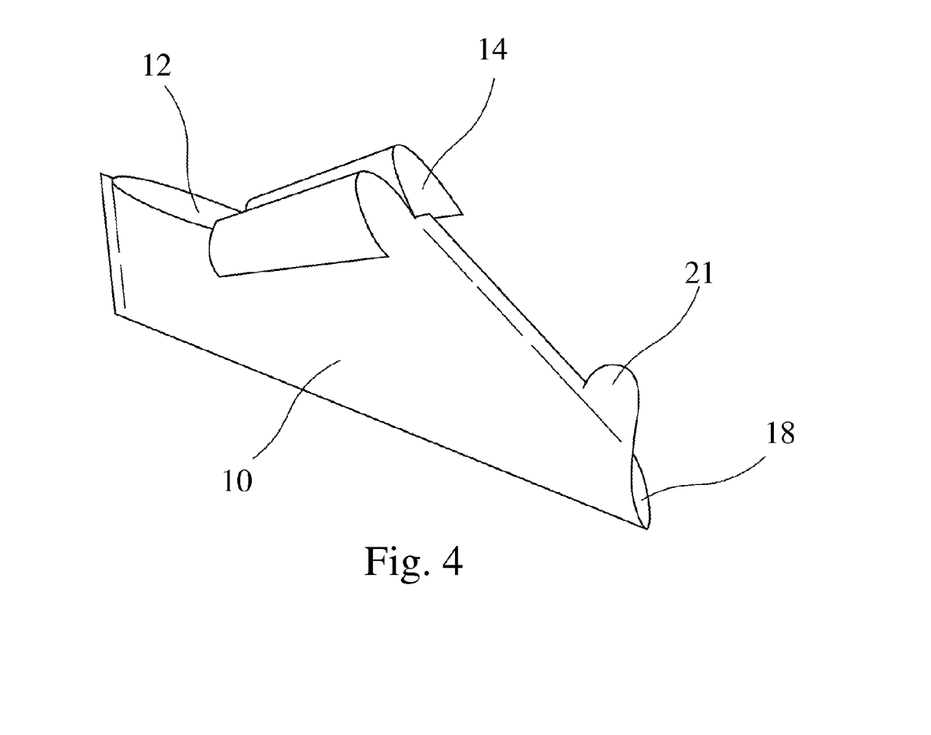

Referring to FIGS. 2A to 2B, a zipper 16 is provided just below the open top 12 so that after use an individual may pull the zipper 16 to close the bag 10 for disposal in an outdoor environment without the provision of public toilet. The supporting members 14 may have configurations (see FIGS. 2A to 2B) other than the one shown in FIGS. 1A, 1B and 1C. The supporting members 14 in FIGS. 2A and 2B are formed of soft materials. The supporting members 14 are formed to be m shape structures with stiffened material so that the bag 10 may be hanged on the fingers and different sizes of fingers are all applicable. Alternatively, adhesive material 13 is applied outside of the open top 12 so that the bag 10 may be adhered onto the fingers. Still alternatively, the supporting members 14 are formed of adhesive material to be ready to adhere onto the fingers. Further alternatively, the supporting members 14 are two fingerstalls so that the fingers of an individual may insert into. The supporting members 14 in FIGS. 2A and 2B are formed of soft membranous material. The bag 10 has an upper portion folded downward to form m shape so that at least one point of the edge of the supporting member 14 can be secured to the bag 10 (see FIG. 2A). Alternatively as shown in FIG. 2B, two separated adhesive material 13 are applied on the finger sides of each supporting member 14 so that supporting members 14 may cover and stick on two fingers in order to let fingers hold on two sides of the open top 12 more effectively. Further, fingers of different sizes all are permitted to do so. Furthermore (see FIG. 2B), a water absorbent layer 15 is formed on an outer surface of each supporting member 14 facing the skin to be adhered thereto. This ensures a leak proof seal to prevent contamination of human body or clothes by the excrement. While different configurations of the supporting members 14 are shown in FIGS. 2A to 2B, other configurations of the supporting members 14 for holding the bag 10 are contemplated by the invention and are within the scope of the invention.

Figure 6:
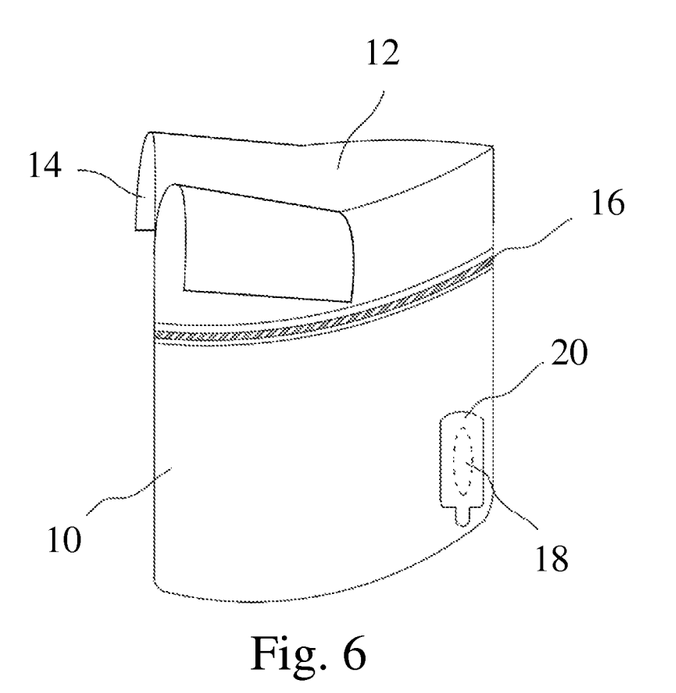
FIG. 6 is another perspective views of the disposable urine bag device.

Referring to FIG. 6, an opening 18 is disposed at a bottom corner of the bag 10. In the embodiment, the opening 18 is provided in a lower portion of one sidewall of the bag 10 proximate to the bottom so that urine in the bag 10 may drain therethrough. Moreover, a valve 20 is mounted on the opening 18 so that collected urine may drain via the valve 20 by regulating the outflow of content in bag 10. The valve 20 is implemented as a zipper for opening or closing the opening 18. The disposable urine bag device of the invention not only facilitates urine collection but also facilitates the pouring of urine from opening 18 into a test tube for examining by controlling the valve 20. While the valve 20 is shown in FIG. 6, other configurations of the valve 20 for controlling the outflow of excrement in bag 10 are contemplated by the invention and are within the scope of the invention.

Figure 5A:
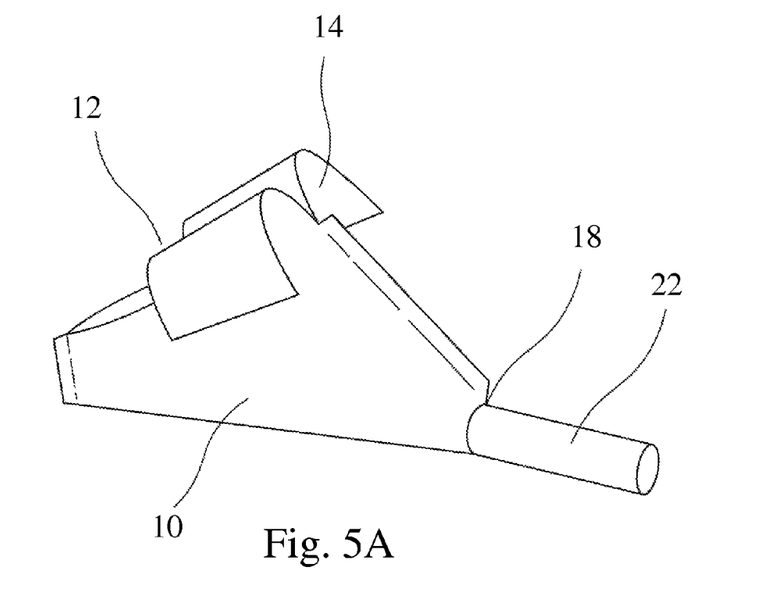
FIGS. 5A and 5B are respectively perspective and environmental views of the urine bag device of FIG. 7 with a pipe connected to the opening.
Figure 5B:
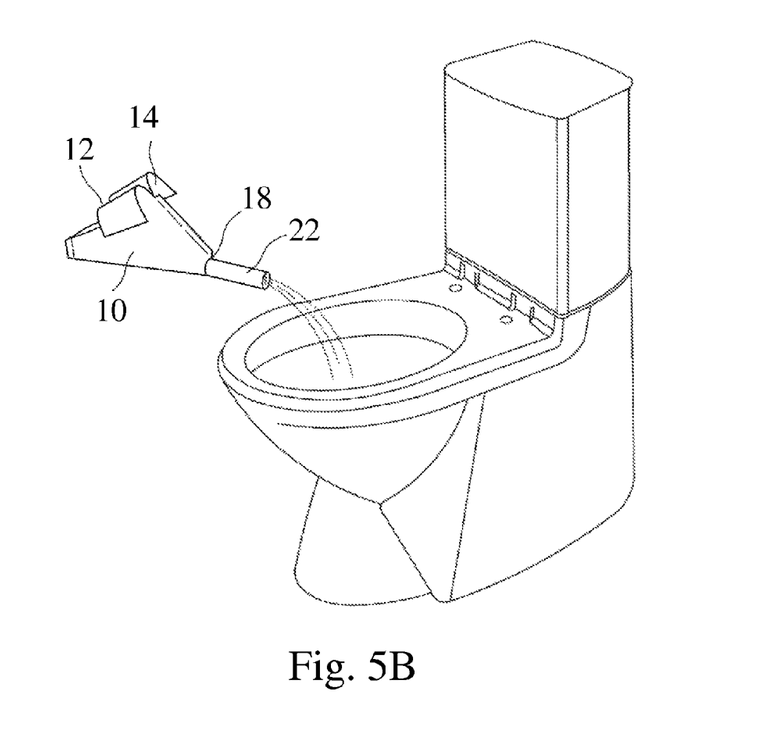
Figure 7:
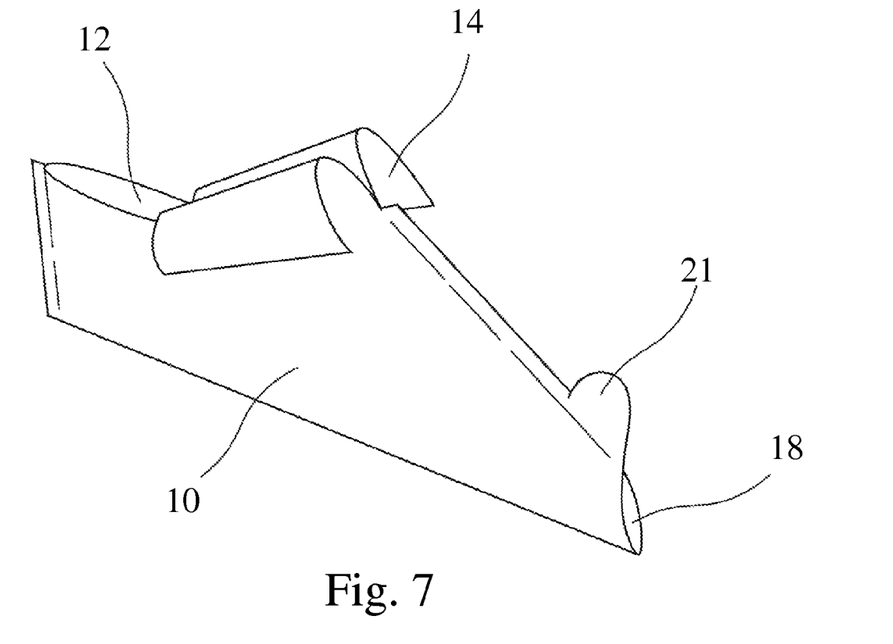
FIG. 7 is a perspective view of a disposable urine bag device according to a second embodiment of the invention.

Referring to FIG. 7, a disposable urine bag device in accordance with a second embodiment of the invention is shown. An individual, especially a woman, may hold back urine if the available public toilet is unhygienic. Advantageously, the bag 10 is modified as a quadrilateral or polygonal shape with a protruded angle at the bottom and an opening 18 formed at the protruded front end so that an individual may pass urine into the bag 10 in urination while in standing position. Further, urine flows into a toilet via the forwardly extended opening 18. Such configuration enables an individual to keep the urine more away from the body. An obtuse angle 11 is existed between the supporting members 14 and the rear portion of the open top 12. The obtuse angle 11 is on the side contacted with a human body. The supporting members 14 are located at two sides of the front portion of the open top 12 of the bag 10 respectively. The obtuse angle 11 is fit with the outline of the vulva. It is particularly suitable for the women use. Moreover, a tab 21 projects upward out of the opening 18 so that an individual may hold the tab 21 to direct the flow of urine through the opening 18. As shown in FIGS. 5A and 5B in conjunction with FIG. 7, a short pipe 22 can be connected to the opening 18 for correctly directing urine in the bag 10 to toilet. This enables an individual to avoid sitting on a dirty toilet seat while urinating. The flow exit of the pipe 22 is further away from the individual so that urine may not drop onto the clothes.

The disposable urine bag device of the invention has the following advantages: It can not only collect urine but also feces. Two fingers are allowed to insert into the supporting members to position the bag and adjust size of the open top of the bag in order to completely cover the excretory orifices of human being. It is easy to seal, carry and dispose after use. It facilitates pouring urine into a test tube. Finally, it can collect and direct the urine into a toilet.

In view of above, the disposable urine bag device of the invention employs two supporting members for fingers insertion so as to permit an individual to position the bag and adjust size of the open top of the bag. Further, the disposable urine bag device can be held against the excretory orifices more precisely with sufficient pressure to form a seal. Hence, it can accurately collect excrement without leaking. An individual, especially a woman, may use the disposable urine bag device to urinate in a standing position or sitting position as in an automobile.

While the invention has been described in terms of embodiments, those skilled in the art will recognize that the invention can be practiced with modifications within the spirit and scope of the appended claims.

What is claimed is:

1. A disposable urine bag device comprising:
a bag having an open top, two sidewalls and a bottom edge which is distant from the open top; and
two supporting members coupled to opposing sides of a front portion of the open top of the bag configured for accepting fingers of a user, each supporting member having an outer surface and an inner surface, the inner surface of each supporting member being applied with an adhesive material, the adhesive material configured for adhering to one of the fingers, the two supporting members thereby enabling positioning of the bag and adjusting size of the open top of the bag to cover the excretory orifices of the user's body,
wherein each supporting member is integrally formed with an upper portion of the bag, wherein the bag during use is closely conformed for positioning against the user's body.

2. The disposable urine bag device of claim 1, further comprising a zipper positioned below the open top of the bag.

3. The disposable urine bag device of claim 2, further comprising a patch-type valve mounted on one sidewall of the bag.

4. The disposable urine bag device of claim 1, further comprising an opening located on one sidewall of the bag.

5. The disposable urine bag device of claim 4, wherein the opening is disposed at a bottom corner.

6. The disposable urine bag device of claim 4, further comprising a pipe connected to the opening for draining excrement in the bag.

7. The disposable urine bag device of claim 1, wherein the bag is made of thermoplastic material or paper.

8. The disposable urine bag device of claim 1, wherein the supporting members are formed as m shape means for hanging the finger.

9. The disposable urine bag device of claim 1, wherein each supporting member comprises a water absorbent layer formed on the outer surface facing the skin.

10. The disposable urine bag device of claim 1, wherein the bag is formed as a quadrilateral or polygonal shape with a protruded angle at the bottom and with an opening at the protruded angle.

11. The disposable urine bag device of claim 4, further comprising a tab projecting upward out of the opening.

12. The disposable urine bag device of claim 1, wherein the front portion of the open top of the bag has a higher elevation than a rear portion of the open top of the bag, the supporting members are located on two sides of the front portion of the open top respectively, and an obtuse angle exists between the supporting members and the rear portion of the open top.

* * * * *